United States Patent
Bod et al.

Patent Number: 5,478,949
Date of Patent: Dec. 26, 1995

[54] PROCESS FOR PREPARING ONDANSETRON

[75] Inventors: Peter Bod, Gyömrö; Kálmán Harsányi, Budapest; Ferenc Trischler, Budapest; Éva Fekecs, Budapest; Attila Csehi, Göd; Béla Hegedüs, Budapest; Éva Mersich née Donát, Budapest; Györgyi Szabó née Komlósi, Budapest; Erika Horváth née Sziki, Budapest, all of Hungary

[73] Assignee: Richter Gedeon Vegyeszeti Gyar Rt., Budapest, Hungary

[21] Appl. No.: 344,871

[22] Filed: Nov. 25, 1994

Related U.S. Application Data

[62] Division of Ser. No. 135,407, Oct. 13, 1993, Pat. No. 5,416,221.

[30] Foreign Application Priority Data

Oct. 14, 1992 [HU] Hungary .................. 3222/92
Oct. 14, 1992 [HU] Hungary .................. 3223/92

[51] Int. Cl.[6] ............................. C07D 403/06
[52] U.S. Cl. ............................. 548/311.4
[58] Field of Search ..................... 548/311.4

[56] References Cited

U.S. PATENT DOCUMENTS 4,939,144  7/1990  Coates et al. .......... 548/311.4
4,957,609  9/1990  Godfrey et al. ........ 548/311.4

Primary Examiner—Robert W. Ramsuer
Attorney, Agent, or Firm—Keil & Weinkauf

[57] ABSTRACT

The invention relates to carbazolone derivatives of the formula

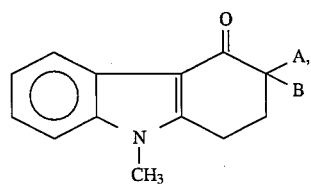

wherein
A stands for a group of formula

—CH$_2$—R    (V), wherein R means a hydroxyl or 2-methyl-1H-imidazol-1-yl group;
B represents a group of formula

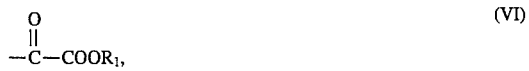

wherein R$_1$ means hydrogen or a methyl or ethyl group; or
A and B together form a group of formula

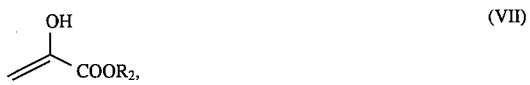

wherein R$_2$ means a methyl or ethyl group; or
A and B together form a group of formula

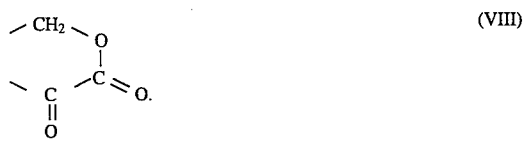

The above compounds are useful intermediates in the synthesis of ondansetron of formula

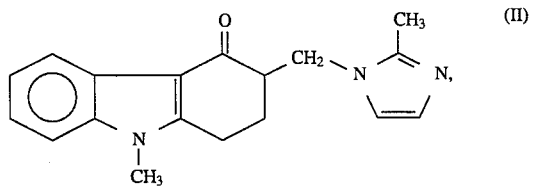

chemically 9-methyl-3-[(2-methyl-1H-imidazol-1-yl)methyl]-1,2,3,9-tetrahydro-4H-carbazol-4-one.

The invention further relates to a novel process for the preparation of compounds of the formula (I), wherein A and B are the same as in formula (I) but B may be also hydrogen. Thus, this novel process is suitable for the preparation of ondansetron itself.

8 Claims, No Drawings

PROCESS FOR PREPARING ONDANSETRON

This is a divisional of application Ser. No. 08/135,407, filed Oct. 13, 1993, now U.S. Pat. No. 5,416,221.

The invention relates to novel carbazolone derivatives of formula

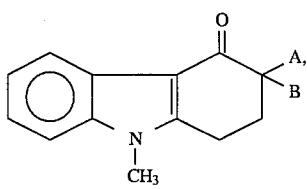

wherein

A stands for a group of formula

   (V), wherein R means a hydroxyl or 2-methyl-1H-imidazol-1-yl group;

B represents a group of formula

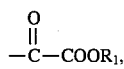   (VI)

wherein $R_1$ means hydrogen or a methyl or ethyl group; or

A and B together form a group of formula

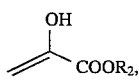   (VII)

wherein $R_2$ means a methyl or ethyl group; or

A and B together form a group of formula

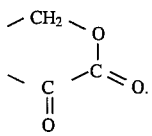   (VIII)

Furthermore, the invention relates to a process for the preparation of the above compounds.

The compounds of formula (I) are valuable intermediates in the synthesis of 9-methyl-3-[(2-methyl-1H-imidazol-1-yl)methyl]-1,2,3,9-tetrahydro-4H-carbazol-4-one of formula

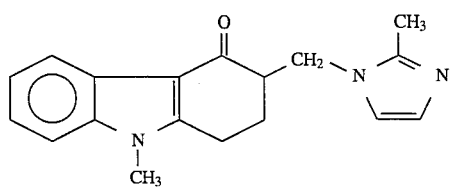

(generic name: ondansetron) and its acid addition salts, preferably the hydrochloride dihydrate.

Thus, the invention relates also to a novel process for the preparation of ondansetron of the formula (II).

Due to its selective 5-HT$_3$ antagonistic effect, ondansetron is an excellent antiemetic drug, inhibiting vomiting and nausea by decreasing the gastric motility, mainly during cancer chemotherapy (see GB patent specification No. 2,153,821).

Several processes have been published for the preparation of ondansetron.

According to a process described in the published European patent application No. 219,929, the imidazolyl-alkyl side chain is introduced by a three-step synthesis onto the methylene group neighbouring the oxo group of the 1,3-cyclohexanedione monoenol ether used as starting substance. After that the enol ether group is replaced by a 2-methyl-2-phenylhydrazino group and the phenylhydrazone obtained is subjected to a Fischer's indole synthesis. The drawbacks of this process, comprising five steps, reside in the use of dangerous and expensive reagents (butyl lithium, dimethylmethyleneammonium iodide, 1-methyl-1-phenylhydrazine) and technological steps, which result a moderate yield and which are difficult to carry out, in some cases, and to increase to industrial scales (c.f. column chromatography, temperature of −70° C.). The overall yield of ondansetron is only 9.57%, calculated for 1,3-cyclohexanedione monoenol ether.

According to another method described in the published European patent application No. 221,629, after reacting an imidazolylalkyl-1,3-cyclohexanedione monoenol ether with 2-iodoaniline, the enamine obtained is cyclized with palladium(II) acetate. The indole-N atom of the product thus formed is methylated in the last step. The drawbacks of this process are the same as those of the former one. The overall yield of ondansetron is at most 1.0%, calculated for 1,3-cyclohexanedione monoenol ether used as starting substance.

According to the above-said GB patent specification No. 2,153,821 (which is equivalent to the Hungarian patent specification No. 193,592), 3-(dimethylaminomethyl)-9-methyl-1,2,3,9-tetrahydro-4H-carbazol-4-one is used as starting substance, which is heated with 2-methylimidazole to obtain ondansetron. However, the starting tertiary amine is similarly basic in character as ondansetron, which causes separation difficulties in the purification of the final product.

Another important disadvantage of this process consists therein that no teaching for the preparation and characterization of the starting tertiary amine compound can be found either in the specification itself or in the literature.

Peculiarly, the above-said patent specification indicates this tertiary amine to be known per se and, in addition, ondansetron can be prepared therefrom in an other way, too. After quaternizing the tertiary amine with methyl iodide, trimethylamine is split off from the obtained methoiodide by Hofmann's elimination reaction to give 9-methyl-3-methylene-1,2,3,9-tetrahydro-4H-carbazol-4-one. The thus-obtained electrophilic conjugated enone is subjected to an addition reaction with 2-methylimidazole (see Example 8 of the specification). The surprisingly moderate yield of 43.2% of the reaction shows that the significance of this simple direct addition, starting from the separated enone, should not be overestimated.

However, the reaction of 2-methylimidazole with the said tertiary amine compound (c.f. Example 7) results in a good yield of ondansetron (100% of crude product, 82% of recrystallized product). These data suggest that the reaction mechanism of the last step in the known synthesis of ondansetron is decisively not an elimination-addition reaction in its character but has another type, i.e. N,N'-transamination by direct substitution.

The present invention is aimed at developing a preparation process, in the course of which a pure final product can be obtained from novel intermediates through selective reactions, being easy to carry out and increase to an industrial scale, whereby the above drawbacks can be eliminated.

The invention is based on the surprising discovery that any of the new alkoxalylated 4-carbazolones of formula

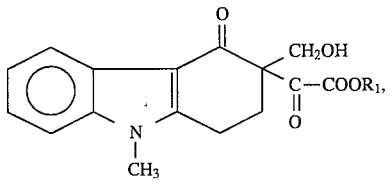

(Ib)

wherein R₁ means a methyl or ethyl group, or formula

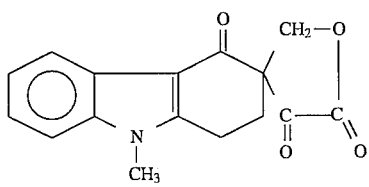

(Ic)

can N-monoalkylate 2-methylimidazole of formula

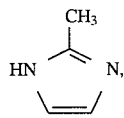

(IV)

and the obtained intermediate of formula

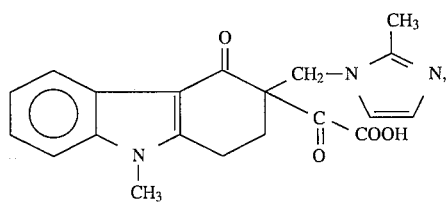

(Id)

chemically 9-methyl-3-[(2-methyl-1H-imidazol-1-yl)methyl]-1,2,3,9-tetrahydro-4H-carbazol-4-one-3-glyoxylic acid, can be converted into ondansetron of the formula (II) by dealkoxalylating with a nucleophilic reagent.

The surprising character of this solution can be explained as follows:

It is well-known that the N-acylation of imidazoles can easily be carried out in a non-aqueous medium by using strong acylating agents, e.g. reactive esters (Alan E. Katritzky, Charles W. Rees: "Comprehensive Heterocyclic Chemistry" Vol 5, p. 390-393) Based on this one could expect that the substituted glioxylic acid esters of the formula (Ib) or the lactone of the formula (Ic), both being strong 10 acylating agents, would acylate 2-methylimidazole of the formula (IV) to give the following compound:

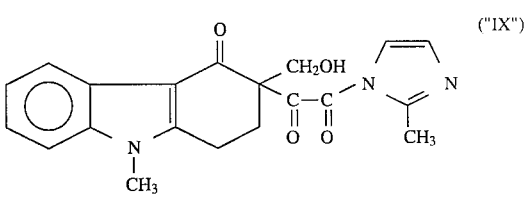

("IX")

In an entirely surprising manner the methylene part of the C-hydroxymethyl group was attached to the nitrogen atom of 2-methylimidazole in an N-alkylation reaction, giving the compound of the formula (Id), being sterically more dense, rather than the N-acylimidazole of the formula ("IX").

Thus, the present invention relates to novel compounds of formula

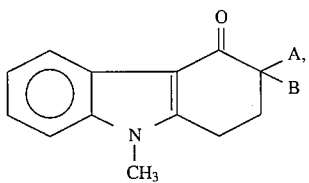

(I)

wherein
A stands for a group of formula

$-CH_2-R$ (V), wherein R means a hydroxyl or 2-methyl-1H-imidazol-1-yl group;

B represents a group of formula

(VI)

$$\begin{matrix} O \\ \| \\ -C-COOR_1, \end{matrix}$$

wherein R₁ means hydrogen or a methyl or ethyl group; or

A and B together form a group of formula

(VII)

wherein R₂ means a methyl or ethyl group; or

A and B together form a group of formula

(VIII)

The new compounds are as follows:
3-ethoxalyl-9-methyl-1,2,3,9-tetrahydro-4H-carbazol-4-one,
methyl 3-hydroxymethyl-9-methyl-1,2,3,9-tetrahydro-4H-carbazol-4-one-3-glyoxylate,
ethyl 3-hydroxymethyl-9-methyl-1,2,3,9-tetrahydro-4H-carbazol-4-one-3-glyoxylate,
3-hydroxymethyl-9-methyl-1,2,3,9-tetrahydro-4H-carbazol-4-one-3-glyoxilic acid lactone and
9-methyl-3-[(2-methyl-1H-imidazol-1-yl )methyl]-1,2,3,9-tetrahydro-4H-carbazol-4one-3-glyoxylic acid.

Further, the invention relates also to a process for the preparation of the partially novel, partially known compounds of formula

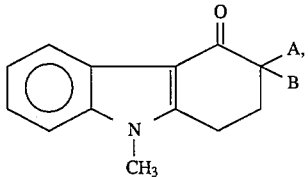
(I)

wherein

A stands for a group of formula

—CH$_2$—R  (V), wherein R means a hydroxyl or 2-methyl-1H-imidazol-1-yl group;

B represents hydrogen or a group of formula

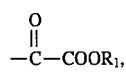
(VI)

wherein R$_1$ means hydrogen or a methyl or ethyl group; or

A and B together form a group of formula

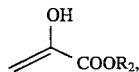
(VII)

wherein R$_2$ means a methyl or ethyl group; or

A and B together form a group of formula

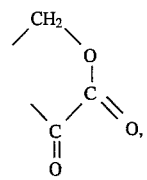
(VIII)

which comprises a) reacting the ketone of formula

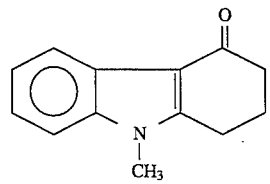
(III)

with a di(C$_{1-2}$alkyl)oxalate in the presence of a basic agent in order to obtain a novel compound of the formula

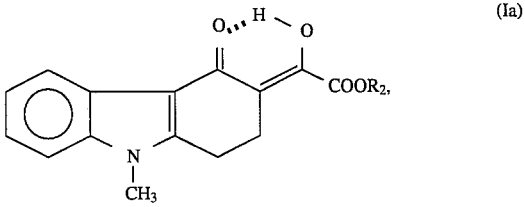
(Ia)

wherein R$_2$ stands for a methyl or ethyl group;

b) reacting a compound of the formula (Ia), wherein R$_2$ is as defined in step a) above, with formaldehyde in the presence of a basic catalyst in a non-acidic protic solvent in order to obtain a novel compound of the formula (Ib), wherein R$_1$ is a methyl or ethyl group; or reacting a compound of the formula (Ia), wherein R$_2$ is as defined in step a) above with formaldehyde in the presence of a basic catalyst in an aprotic solvent in order to obtain the novel compound of the formula (Ic);

c) reacting a compound of the formula (Ib), wherein R$_1$ is as defined in step b) above, or the compound of the formula (Ic) with 2-methylimidazole of the formula (IV) in order to obtain the novel compound of the formula (Id);

d) reacting the compound of the formula (Id) with a base, preferably an alkali metal carbonate or hydroxide, in order to obtain ondansetron of the formula (II), and, if desired, converting ondansetron of the formula (II) into its pharmaceutically acceptable acid addition salt.

According to variant b) of the above process, the compounds of formula (Ia), wherein R$_2$ is as defined above, are reacted with 1 to 2 moles, preferably 1.2 to 1.6 moles, of formaldehyde in the presence of not more than 0.2 mole of a basic catalyst, preferably an alkaline metal carbonate or a trialkyl amine. The reaction is carried out preferably in methanol or ethanol if a compound of the formula (Ib) is to be prepared. If the compound of the formula (Ic) is to be prepared, the reaction with formaldehyde is carried out preferably in a dipolar aprotic solvent like acetonitrile or acetone. When in variant c) of the process of the invention a compound of the formula (Ib), wherein R$_1$ means a methyl or an ethyl group, or the compound of the formula (Ic) is used as starting substance, the oxalyl group is removed by alcoholysis of the C—C bond in the presence of a C$_{1-4}$alkanol and the group cleaved off is bound by salt formation with a base being stronger than 2-methylimidazole, preferably with triethylamine.

2-Methylimidazole is used in an amount of 1.0 to 3.0 moles, preferably 1.5 to 2.0 moles, calculated for a compound of the formula (Ib), wherein R$_1$ means a methyl or ethyl group, or for the compound of the formula (Ic).

When carrying out variant c) of the process of the invention, a compound of the formula (Ib) or (Ic) is heated with 2-methylimidazole in an aprotic solvent until the reaction becomes complete. Then in variant d) the oxalyl group is removed by a nucleophilic agent to obtain the target compound of the formula (II).

According to a preferred embodiment of variant c) of the process of the invention, 1.0 to 3.0 moles, preferably 1.5 to 2.0 moles of 2-methylimidazole, 1.0 to 2.0 moles of ethanol and a base stronger than 2-methylimidazole, advantageously 1.1 to 1.5 moles of triethylamine, each calculated for 1 mole of a compound of the formula (Ib) or (Ic), are used in an ether-type solvent such as dioxane, or in a dipolar aprotic solvent, preferably dimethylformamide, dimethylsulfoxide or sulfolane. The reaction requiring heating is carried out at a temperature between 70° C. and 200° C. preferably between 100° C. and 150° C, for 0.25 to 20 hours, advantageously 0.25 to 5 hours, then the product of the formula (II) is precipitated by dilution with water or by salt formation and isolated by filtration.

The compound of the formula (II) is obtained from the compound of the formula (Id) by using an aqueous alkaline metal hydroxide or alkaline metal carbonate solution at a temperature from 20° C. to 100° C., preferably a potassium hydroxide or carbonate solution at 30 to 70° C. The compound of the formula (II) obtained in the free base form may be converted into its monohydrochloride dihydrate in a way known per se.

In comparison to the processes known in the art the advantages of the process according to the invention are as follows.

a) The process consists of reactions easy to carry out and to increase up to industrial scales.

b) The alkoxalyl group proves to be an excellent adjuvant function for the selective introduction of the imidazolylmethyl side chain, which is later easily split off in the form of an oxalate salt, in some cases spontaneously, in situ in the reaction mixture.

c) The reactions can be performed in very good yields of 70 to 90% to result in well-isolable and well-characterizable crystalline substances in all cases.

d) An additional advantage appears also therein that the intermediates of the reaction sequence do not contain any basic group; therefore, the final product is easy to purify.

Thus, the isolation of a pure final product becomes extremely simple since none of the possible or actual impurities contains a basic group. In contrast, the synthesis disclosed in the above-cited GB patent specification No. 2,153,821 proceeds through the intermediate 3-(dimethylaminomethyl)-carbazol-4-one, i.e. through a substance basic in its character and difficult to remove.

The invention is illustrated in detail by the following Examples.

EXAMPLE 1

Preparation of 3-ethoxalyl-9-methyl-1,2,3,9-tetrahydro-4H-carbozol-4-one [compound of formula (Ia), wherein $R_2$ means an ethyl group]

3.0 g (0.13 mole) of sodium metal are portionwise added to a stirred mixture containing 19.93 g (0.1 mole) of 9-methyl-1,2,3,9-tetrahydro-4H-carbazol-4one of formula (III), 19.0 g (0.13 mole) of diethyl oxalate, 2 g of ethanol and 200 ml of dioxane. The slightly warming reaction mixture is stirred at 40° to 50° C. for 4 hours, then 16 g of glacial acetic acid and finally 200 ml of water are added thereto at room temperature. After filtering off the yellow crystalline suspension, the precipitate is washed with water and dried to give the title compound in a yield of 24 g (80.2%), m.p.: 118°–120° C.

The active ingredient content of the product amounts to 98.4% based on potentiometric titration with sodium hydroxide solution.

IR spectrum (KBr), νmax:

| | |
|---|---|
| OH | 3600–2000 cm$^{-1}$ |
| C=O (ester) | 1727 cm$^{-1}$ |
| O=C—C=C | 1590 cm$^{-1}$ |
| | 1578 cm$^{-1}$ |
| C—O—C (ester) | 1213 cm$^{-1}$ |
| =C—OH (enol) | 1185 cm$^{-1}$ |
| Ar—H (bending) | 754 cm$^{-1}$ |

$^1$H-NMR (DMSO-d6) δppm:

| | |
|---|---|
| C$\underline{H_3}$—CH$_2$— | 1.47 (3H, t) |
| —C$\underline{H_2}$— | 2.75 (2H, t) |
| —C$\underline{H_2}$— | 3.12 (2H, t) |
| CH$_3$—N | 3.60 (3H, s) |
| CH$_3$—C$\underline{H_2}$—O | 4.36 (2H, q) |
| Ar—H | 7.24 (2H, m) |
| | 8.00 (1H, dd) |
| | 8.13 (1H, dd) |

EXAMPLE 2

Preparation of 3-ethoxalyl-9-methyl-1,2,3,9-tetrahydro-4H-carbazol-4-one [compound of formula (Ia), wherein $R_2$ means an ethyl group]

After adding 7.1 g (0.13 mole) of solid sodium methoxide to a stirred mixture containing 19.93 g of the ketone of formula (III) (for the chemical name see Example 1), 19 g of diethyl oxalate and 200 ml of 1,2-dimethoxyethane, the process described in Example 1 is followed to obtain 23.1 g (77.2%) of the title compound, m.p.: 117°–120° C.

The titrimetrically determined active agent content of the product is 97.9%.

The spectroscopical data of the product are the same as described in Example 1.

EXAMPLE 3

Preparation of methyl 3-hydroxymethyl9-methyl-1,2,3,9-tetrahydro-4-H-carbazol-4-one-3-glyoxylate After dropwise adding 0.2 g of triethylamine to a stirred suspension of 3.00 g (0.01 mole) of the ethoxalyl compound of formula (Ia), wherein $R_2$ is an ethyl group (chemically 3-ethoxalyl-9-methyl-1,2,3,9-tetrahydro-4H-carbazol-4-one), and 0.45 g of paraformadehyde in 20 ml of methanol, the reaction mixture is heated at 55° to 60° C. for 1 hour. After cooling the reaction mixture is filtered off, the precipitate is washed with methanol and dried to give 2.45 g (78.7%) of the title compound, m.p.: 238°–242° C. (with decomposition).

IR spectrum (KBr), νmax:

| | |
|---|---|
| O—H | 3350 cm$^{-1}$ (broad) |
| C=O | 1782 cm$^{-1}$ (alpha-oxo + ester) |
| | 1628 cm$^{-1}$ (alpha-oxo + ester) |
| C—O—C | 1137 cm$^{-1}$ (ester) |
| C—OH | 1056 cm$^{-1}$ |
| Ar—H (bending) | 744 cm$^{-1}$ |

$^1$H-NMR (DMSO-d 6 ) δ ppm:

| | |
|---|---|
| —CH$_2$— | 2.1 (1H, m) |

| | |
|---|---|
| —CH₂— | 2.55 (1H, m) |
| | 2.98 (1H, m) |
| | 3.20 (1H, m) |
| CH₃—O— | 3.25 (3H, s) |
| CH₃—N | 3.68 (3H, s) |
| —C—CH₂OH | 3.99 (1H, d) |
| | 4.50 (1H, d) |
| Ar—H | 7.21 (2H, m) |
| | 7.47 (1H, dd) |
| | 8.00 (1H, dd) |

EXAMPLE 4

Preparation of ethyl 3-hydroxymethyl-9-methyl-1,2,3,9-tetrahydro-4-H-carbazol-4-one-3-glyoxylate The process described in EXAMPLE 3 is followed, except that ethanol is used instead of methanol. In this way 2.65 g (80.55%) of title compound are obtained, m.p.: 240°–245° C. (with decomposition).

IR spectrum: the characteristic bands are identical with those of the methyl ester.

¹H-NMR ( DMSO-d 6 ) δ ppm:

| | |
|---|---|
| CH₃CH₂— | 1.15 (3H, t) |
| —CH₂— | 2.05 (1H, m) |
| | 2.58 (1H, m) |
| CH₂— | 2.97 (1H, m) |
| | 3.18 (1H, m) |
| O—CH₂—CH₃ | 3.45 (2H, q) |
| CH₃—N | 3.68 (3H, s) |
| —C—CH₂OH | 3.94 (1H, d) |
| | 4.48 (1H, d) |
| Ar—H | 7.21 (2H, m) |
| | 7.47 (1H, dd) |
| | 8.00 (1H, dd) |

EXAMPLE 5

Preparation of 3-hydroxymethyl-9-methyl-1,2,3,9-tetrahydro-4H-carbazol-4-one-3-glyoxylic acid lacton [compound of formula (Ic)]

After adding 0.1 g of triethylamine to a stirred suspension containing 3.00 g (0.01 mole) of the ethoxalyl compound of the formula (Ia), wherein R₂ means an ethyl group (for the chemical name see EXAMPLE 3) in 20 ml of acetone, 1.13 g (0.015 mole) of formol solution are dropwise added to the mixture. The suspension becomes clear within 1 to 2 minutes and crystals begin to precipitate. After further stirring at 35° to 40° C. for one hour, the reaction mixture is cooled down to room temperature, filtered off, the precipitate is washed with 50% acetone and dried to give 2.10 g (74.2%) of the title compound, m.p.: 242°–244° C.

IR spectrum (KBr), νmax:

| | |
|---|---|
| O—H | 1794 cm⁻¹ (lactone) |
| C=O | 1782 cm⁻¹ (alpha-oxo) |
| C=O | 1642 cm⁻¹ (carbazol-4-one) |
| C—O—C | 1259 cm⁻¹ |
| Ar (skeleton vibration) | 1579 cm⁻¹ |
| Ar—H (bending) | 755 cm⁻¹ |

¹H-NMR (DMSO-d6) δ ppm:

| | |
|---|---|
| —CH₂— | 2.4 (1H, m) |
| | 2.75 (1H, m) |
| —CH₂— | 3.09 (1H, m) |
| | 3.78 (1H, m) |
| CH₃—N— | 3.75 (3H, s) |
| —C—CH₂O | 4.53 (1H, d) |
| | 5.04 (1H, d) |
| Ar—H | 7.22 (2H, m) |
| | 7.53 (1H, dd) |
| | 7.92 (1H, dd) |

EXAMPLE 6

Preparation of 3-hydroxymethyl-9-methy-1,2,3,9-tetrahydro-4H-carbazol-4-one-3-glyoxylic acid lactone [compound of formula (Ic)]

To a suspension containing 29.93 g (0.10 mole) of 3-ethoxalyl-9-methyl-1,2,3,9-tetrahydro-4H-carbazol-4-one and 10.5 g (0.14 mole) of formol solution in 200 ml of acetonitrile, 1.0 g (0.0072 mole) of potassium carbonate is added. The reaction mixture is stirred at 30° to 35° C. for one hour. Subsequently, the process described in Example 5 is followed to obtain 22.46 g (75.04%) of the title compound, m.p.: 240°–243+ C.

The spectroscopic data of the product are identical with those of the product of EXAMPLE 5.

EXAMPLE 7

Preparation of ethyl 3-hydroxymethyl-9-methyl-1,2,3,9-tetrahydro-4H-carbazol-4-one-glyoxylate To a mixture containing 0.85 g (0.003 mole) of 3-hydrfoxymethyl-9-methyl-2,3,9-tetrahydro-4H-carbazol-4-one-3-glyoxylic acid lactone of the formula (Ic) and 18.0 of ethanol, 0.2 g of concentrated sulfuric acid is dropwise added under stirring. The reaction mixture is boiled under reflux for 3 hours, then cooled down and filtered off. The precipitate is washed with ethanol and dried to give 0.35 g (35.43%) of the title compound, m.p.: 241°–245° C. (with decomposition).

The spectroscopic data of the product are identical with those of the product of Example 4.

EXAMPLE 8

Preparation of ondansetron base (chemically 9-methyl-3-[(2-methyl-1-H-imidazol-1-yl)methyl]-1,2,3,9-tetrahidro-4-H-carbazol-4-one)

A mixture containing 2.83 g (0.01 mole) of 3-hydroxymethyl-9-methyl-2,3,9-tetrahydro-4H-carbazol-4-one-3 -glyoxylic acid lactone of the formula (Ic), 15 ml of dioxane, 1.32 g of triethylamine, 1.0 g of ethanol and 1.64 g (0.02 mole) of 2-methylimidazole is boiled under reflux while stirring for 5 hours. Thereafter, the reaction mixture is diluted with 45 ml of water and cooled down. The precipitate is filtered off, washed with aqueous dioxane and dried to obtain 2.56 g (87.3%) of the title compound, m.p.: 220°–223° C.

IR spectrum (KBr), νmax:

| | |
|---|---|
| C=O | 1623 cm⁻¹ |
| Ar (skeleton) | 1579 cm⁻¹ |
| N—CH₃ | 1483 cm⁻¹ |
| | 1460 cm⁻¹ |
| HetAr—H (bending) | 781 cm⁻¹ |

-continued

| Ar—H (bending) | 758 cm$^{-1}$ |

$^1$H-NMR (DMSO-d6) β ppm:

| —CH$_2$— | 1.98 (1H, a, axial) |
| | 2.17 (1H, e, equatorial) |
| CH$_3$—C | 2.67 (3H, s) |
| —CH$_2$— | 2.94 (1H, a) |
| | 3.11 (1H, e) |
| —CH— | 3.10 (1H, m) |
| CH$_3$—N | 3.68 (3H, s) |
| —CH—CH$_2$—N | 4.30 91H, dd) |
| | 4.68 (1H, dd) |
| Ar—H | 7.25 (2H, m) |
| | 7.50 (1H, dd) |
| | 8.03 (1H, dd) |
| HetAr—H | 7.57 (1H, d) |
| | 7.67 (1H, d) |

EXAMPLE 9

Preparation of ondansetron base

A mixture containing 3.29 g (0.01 mole) of ethyl 3-hydroxymethyl-9-methyl-1,2,3,9-tetrahydro-4H-carbazol-4-one-3-glyoxylate of the formula (Ib), 10 ml of dimethylsulfoxide, 1.32 g of triethylamine, 0.5 g of ethanol and 1.64 g (0.02 mole) of 2-methylimidazole is stirred at 110° to 120° C. for 3 hours. After diluting the reaction mixture with 40 ml of water, cooling down and filtering off, the precipitate is washed with water and dried to obtain 2.20 g (75%) of the title product, m.p.: 219°–223° C.

The spectroscopic data of the product are in agreement with those of the product of Example 8.

EXAMPLE 10

Preparation of ondansetron base
a) Preparation of 9-methyl-3-[(2-methyl-1H-imidazol-1-yl-)methyl]-1,2,3,9-tetrahydro-4H-carbazol-4-one-glyoxylic acid [compound of formula (Id)]

A mixture containing 2.83 g (0.01 mole) of 3-hydroxymethyl-9-methyl-1,2,3,9-tetrahydro-4H-carbazol-4-one-3-glyoxylic acid lactone [compound of the formula (Ic)]and 1.64 g (0.02 mole) of 2-methylimidazole in 6.0 ml of sulfolane (tetramethylenesulfone) is heated in an oil bath of 150 to 160° C. for 15 minutes while stirring. After cooling down and diluting with 60 ml of acetone the precipitate is filtered off, washed with acetone and dried to give 0.95 g of the title compound, m.p.: 190°–200° C. (with decomposition). The active agent content of this product measured by titration with perchloric acid in glacial acetic acid was found to be 96%. In the combined filtrate of the reaction, ondansetron could be detected by thin layer chromatography. The most important characteristics of the title product are as follows:

IR spectrum (KBr), vmax:

| X—H | 3440 cm$^{-1}$ |
| | 2650 cm$^{-1}$ |
| | 2550 cm$^{-1}$ |
| | 1973 cm$^{-1}$ |
| C=O | 1628 cm$^{-1}$ (alpha-oxo + carbazol-4-one) |
| —COO— | 1595 cm$^{-1}$ |

| Ar—H (bending) | 763 cm$^{-1}$ | b) Preparation of ondansetron base

A suspension containing 0.73 g (0.002 mole) of the product of the formula (Id) prepared in the preceding step a) and 0.40 g (0.0061 mole) of 85% potassium hydroxide in 20 ml of water is stirred at 45° to 50° C. for one hour. After cooling down and filtering off the suspension, the precipitate is thoroughly washed with water and dried to give 0.50 g (85.32%) of the title product, m.p.: 223°–225° C.

The spectroscopic data of the product are in agreement with those of the product of Example 8.

The active agent content of the product was found to be 97.6% based on the potentiometric titration with hydrochloric acid.

EXAMPLE 11

Preparation of 9-methyl-3-[(2-methyl-1-H-imidazol-1-yl)methyl]-1,2,3,9-tetrahydro-4H-carbazol-4-one hydrochloride dihydrate The process described in Example 8 is followed, except that after cooling down the reaction mixture to room temperature after boiling, 20 ml of 37% aqueous hydrochloric acid are added thereto. Then, the precipitate is filtered off, washed with isopropanol and dried to obtain 2.40 g (65.6%) of the title salt, m.p.: 178°–180° C.

The active agent content of the product was found to be 100.3% based on potentiometric titration with sodium hydroxide solution.

The theoretical water content is 9.85% (calculated for $C_{18}H_{19}N_3O \cdot HCl \cdot 2H_2O$). The water content measured is 10.03%.

What we claim is:

1. A process for the preparation of ondansetron which process comprises a) reacting the ketone of the formula

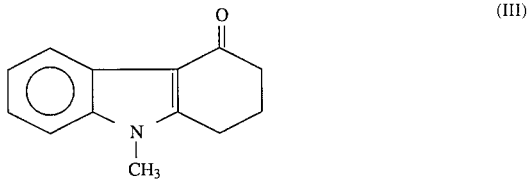

(III)

with a di(C$_{1-2}$alkyl) oxalate in the presence of a basic agent in order to obtain a compound of the formula (Ia),

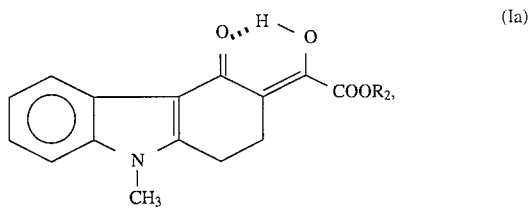

(Ia)

wherein R$_2$ stands for a methyl or ethyl group;

b) reacting a compound of the formula (Ia), wherein R$_2$ is as defined in step a) above, with formaldehyde in the presence of a basic catalyst in a non-acidic protic solvent, in order to obtain a compound of the formula (Ib),

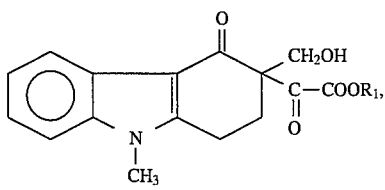 (Ib)

wherein $R_1$ is a methyl or ethyl group; or reacting a compound of the formula (Ia), wherein $R_2$ a is as defined in step a) above, with formaldehyde in the presence of a basic catalyst in an aprotic solvent in order to obtain the compound of the formula (Ic);

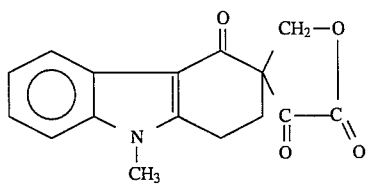 (Ic)

c) reacting a compound of the formula (Ib), wherein $R_1$ is as defined in step b) above, or the compound of the formula (Ic) with 2-methylimidazole of the formula (Iv)

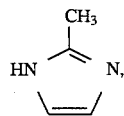 (IV)

to obtain the compound of the formula ( Id ); and

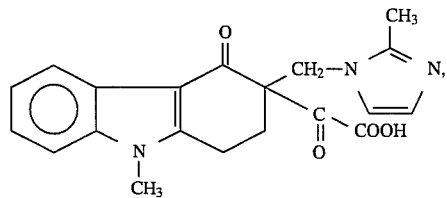 (Id)

d) reacting the compound of the formula (Id) with a base

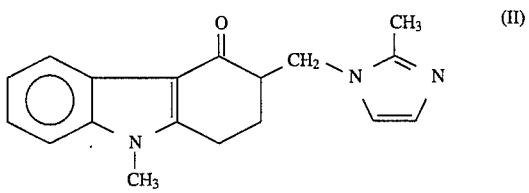 (II)

to obtain ondansetron of the formula (II),

2. A process as defined in claim 1, variant b), which comprises carrying out the reaction of the compound of the formula (Ia), wherein $R_2$ is as defined above, with formaldehyde by using 1 to 2 moles of formaldehyde in the presence of not more than 0.2 mole of an alkaline metal carbonate or a trialkylamine.

3. A process as defined in claim 1, variant b) for the preparation of the compounds of the formula (Ib), wherein the reaction with formaldehyde is carried out in a $C_{1-2}$alkanol.

4. A process as defined in claim 1, variant b) for the preparation of the compound of the formula (Ic), wherein the reaction with formaldehyde is carried out in a dipolar aprotic solvent.

5. A process as defined in claim 1, variant d), wherein the oxalyl group is split off by alcoholysis of the C-C bond in the presence of a $C_{1-4}$alkanol and the group removed is bound by salt formation with a base stronger than 2-methylimidazole 6. A process as defined in claim 1, variant c) which comprises using 2-methylimidazole in an amount of 1.0 to 3.0 moles, calculated for the compound of the formula (Ib), wherein $R_1$ is a methyl or ethyl group, or for the compound for formula (Ic).

7. A process as defined in claim 1, variant c), wherein an ether-type aprotic solvent or dimethylsulfoxide, sulfolane or dimethylformamide is used as solvent.

8. A process as defined in claim 5, wherein the base stronger than 2-methylimidazole is triethylamine.

* * * * *

UNITED STATES PATENT AND TRADEMARK OFFICE
CERTIFICATE OF CORRECTION

PATENT NO. : 5,478,949

DATED : December 26, 1995

INVENTOR(S) : Bod et al

It is certified that error appears in the above-indentified patent and that said Letters Patent is hereby corrected as shown below:

Column 13, claim 1, line 28, "(Iv)" should be --(IV)--.

Signed and Sealed this

Sixteenth Day of April, 1996

BRUCE LEHMAN

Attest:

Attesting Officer

Commissioner of Patents and Trademarks